(12) United States Patent
Lewandowski et al.

(10) Patent No.: US 7,495,054 B2
(45) Date of Patent: Feb. 24, 2009

(54) CURABLE COMPOSITIONS CONTAINING DITHIANE MONOMERS

(75) Inventors: Kevin M. Lewandowski, Inver Grove Heights, MN (US); Ahmed S. Abuelyaman, Woodbury, MN (US); David J. Plaut, Minneapolis, MN (US); Babu N. Gaddam, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 504 days.

(21) Appl. No.: 11/229,903

(22) Filed: Sep. 19, 2005

(65) Prior Publication Data

US 2007/0066748 A1   Mar. 22, 2007

(51) Int. Cl.
C08L 31/00 (2006.01)
C08L 33/00 (2006.01)
C08F 28/06 (2006.01)

(52) U.S. Cl. ................................ 524/556; 526/256
(58) Field of Classification Search ................ 524/556; 526/256
See application file for complete search history.

(56) References Cited

U.S. PATENT DOCUMENTS

| | | | |
|---|---|---|---|
| 4,259,075 A | 3/1981 | Yamauchi et al. |
| 4,262,072 A | 4/1981 | Wendling et al. |
| 4,298,738 A | 11/1981 | Lechtken et al. |
| 4,324,744 A | 4/1982 | Lechtken et al. |
| 4,385,109 A | 5/1983 | Lechtken et al. |
| 4,499,251 A | 2/1985 | Omura et al. |
| 4,503,169 A | 3/1985 | Randklev |
| 4,537,940 A | 8/1985 | Omura et al. |
| 4,539,382 A | 9/1985 | Omura et al. |
| 4,695,251 A | 9/1987 | Randklev |
| 4,710,523 A | 12/1987 | Lechtken |
| 4,737,593 A | 4/1988 | Ellrich et al. |
| 4,872,936 A | 10/1989 | Engelbrecht |
| 5,130,347 A | 7/1992 | Mitra |
| 5,154,762 A | 10/1992 | Mitra et al. |
| 5,501,727 A | 3/1996 | Wang et al. |
| 5,530,038 A | 6/1996 | Yamamoto et al. |
| 5,545,676 A | 8/1996 | Palazzotto et al. |
| 6,251,963 B1 | 6/2001 | Köhler et al. |
| 6,307,062 B1 | 10/2001 | Caye et al. |
| 6,387,981 B1 | 5/2002 | Zhang et al. |
| 6,458,868 B1 | 10/2002 | Okada et al. |
| 6,495,643 B1 * | 12/2002 | Evans et al. ................. 526/256 |
| 6,572,693 B1 | 6/2003 | Wu et al. |
| 6,669,927 B2 | 12/2003 | Trom et al. |
| 6,765,036 B2 | 7/2004 | Dede et al. |
| 6,794,520 B1 | 9/2004 | Moszner et al. |
| 6,982,288 B2 | 1/2006 | Mitra et al. |
| 7,090,721 B2 | 8/2006 | Craig et al. |
| 7,090,722 B2 | 8/2006 | Budd et al. |
| 2003/0166740 A1 | 9/2003 | Mitra et al. |
| 2003/0166830 A1 * | 9/2003 | Okazaki et al. ............. 528/405 |
| 2003/0181541 A1 | 9/2003 | Wu et al. |
| 2004/0151691 A1 | 8/2004 | Oxman et al. |
| 2004/0206932 A1 | 10/2004 | Abuelyaman |
| 2005/0252413 A1 | 11/2005 | Kangas et al. |
| 2005/0256223 A1 | 11/2005 | Kolb et al. |

FOREIGN PATENT DOCUMENTS

| | | |
|---|---|---|
| EP | 0 173 567 A2 | 3/1986 |
| EP | 0 712 622 B1 | 9/1999 |
| EP | 1 279 692 A1 | 1/2003 |
| EP | 1 051 961 B1 | 2/2006 |
| JP | 2000-154251 | 6/2000 |
| JP | 2001-092130 | 4/2001 |
| JP | 2004-107450 | 4/2004 |
| WO | WO 94/14792 A1 | 7/1994 |
| WO | WO 96/19471 A1 | 6/1996 |
| WO | WO 01/30305 A1 | 5/2001 |
| WO | WO 01/30306 A1 | 5/2001 |
| WO | WO 01/30307 A1 | 5/2001 |
| WO | WO 03/063804 A1 | 8/2003 |

OTHER PUBLICATIONS

Evans et al., "New Free-Radical Ring-Opening Acrylate Monomers", Macromolecules, (1994), pp. 7935-7937, vol. 27, No. 26, American Chemical Society.

Evans et al., "Free-Radical Ring-Opening Polymerization of Cyclic Allylic Sulfides", Macromolecules, (1996), pp. 6983-6989, vol. 29, No. 22, American Chemical Society.

Evans et al., "Free-Radical Ring-Opening Polymerization of Cyclic Allylic Sulfides. 2. Effect of Substituents on Seven- and Eight-Membered Ring Low Shrink Monomers", Macromolecules, (2000), pp. 6722-6731, vol. 33, No. 18, American Chemical Society.

Evans et al., "Free Radical Ring-Opening Polymerization of Cyclic Allylic Sulfides: Liquid Monomers With Low Polymerization Volume Shrinkage", Journal of Polymer Science: Part A: Polymer Chemistry, (2001), pp. 202-215, vol. 39, John Wiley & Sons, Inc.

Odian, "Principles of Polymerization", (1991), p. 108, $3^{rd}$ Edition, John Wiley & Sons, Inc., New York.

Takahashi et al., "Neighboring Group Participation in Organic Redox Reactions. 8. [1] Kinetics and Products of the Aqueous Iodine Oxidation of 3-Hydroxy- and 3-Methoxy-1,5-dithiacyclooctanes" Journal of Organic Chemistry, (1983), pp. 3707-3712, vol. 48, No. 21, American Chemical Society.

Watts et al., "Determination of Polymerization Shrinkage Kinetics in Visible-Light-Cured Materials: Methods Development", Dental Materials, (Oct. 1991), pp. 281-287.

(Continued)

Primary Examiner—William K Cheung
(74) Attorney, Agent, or Firm—Kent S. Kokko

(57) ABSTRACT

The invention features compositions comprising at least one monomer that comprises a cyclic dithiane moiety attached to a (meth)acryloyl moiety. The composition may optionally contain additional polymerizable compounds, such as ethylenically unsaturated compounds, that are typically used in dental compositions.

19 Claims, No Drawings

OTHER PUBLICATIONS

U.S Appl. No. 60/600,658, entitled "Self-adhesive Compositions Including a Plurality of Acidic Compounds", filed Aug. 11, 2004.
U.S. Appl. No. 60/678,986, entitled "Dental Compositions Containing Hybrid Monomers With Low Polymerization Shrinkage", filed Sep. 5, 2005.
U.S. Appl. No. 60/679,265, entitled "Hardenable Dental Compositions With Low Polymerization Shrinkage", filed May 9, 2005.
Partial European Search Report, EP Application No. 06814946.7, filed Sep. 19, 2006.

* cited by examiner

CURABLE COMPOSITIONS CONTAINING DITHIANE MONOMERS

FIELD OF THE INVENTION

The present invention is generally related to curable compositions useful in restorative dentistry. More specifically, the invention relates to curable dental compositions containing cyclic dithiane monomers that exhibit low polymerization shrinkage.

BACKGROUND

Dental composites made from organic resins and fillers are finding increasing use in dental applications, especially in restorative dentistry, due to their excellent aesthetic properties. Typical dental composite resins contain low viscosity di(meth)acrylate monomers, which serve as diluents that facilitate high filler levels. These diluents usually are small molecular weight (meth)acrylates, such as triethyleneglycol dimethacrylate (TEGDMA), which shrink substantially upon polymerization due to their low molecular weight. Polymerization shrinkage can lead to a number of problems in dental applications. For example, it often causes gaps between the composite and the tooth structure, which can lead to post-operative sensitivity, microleakage, enamel edge cracks, and secondary caries.

A number of factors are believed to play a role in polymerization shrinkage. It has been postulated that shrinkages occur as the van der Waals distance between monomers are replaced by covalent bonds and the packing density of the polymers increases in comparison to that of the monomers. Recent efforts have been made to reduce polymeric shrinkage by attempting to minimize such phenomena; however, many of the low-shrink compositions currently available lack the physical, mechanical, and optical properties required for dental applications. Moreover, not all low-shrink compositions are efficiently polymerizable under conditions that are suitable for use in the oral cavity. Thus, despite substantial advancement in this area, polymerization shrinkage remains a significant problem when working with certain types of dental composites. Consequently, there remains a need for new composite materials that exhibit reduced polymeric shrinkage without sacrificing other beneficial properties, such as fracture toughness and aesthetics.

SUMMARY OF THE INVENTION

The present invention features a curable dental composition comprising a polymerizable compound having at least one cyclic dithiane moiety and at least one (meth)acryloyl moiety. In one embodiment, the polymerizable compounds of the invention include those represented by the formulae:

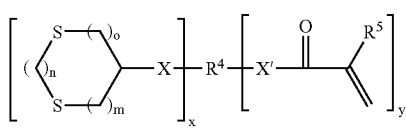

I wherein X and X' are each independently —NR$^1$—, where R$^1$ is an H or a C$_1$-C$_4$ alkyl group or preferably —O—;
each R$^5$ is independently an H, or a C$_1$-C$_4$ alkyl group;
R$^4$ is an organic group having a valence of x+y, such as a polyvalent organic group which can be cyclic, branched, linear, aliphatic, aromatic, or heterocyclic, optionally having catenary (i.e. in chain) nitrogen, and nonperoxidic oxygen atoms, and optionally having one or more organic functional groups including ester, ketone, carbonyl, amide, urea, carbonate and urethane functional groups, preferably R$^4$ is a polyvalent aliphatic or aromatic group, optionally having catenary (i.e. in chain) oxygen atoms, and optionally having one or more organic functional groups including ester, ketone, carbonyl, amide, urea, carbonate and urethane functional groups;
n is 3 to 6, preferably 3 to 5;
m is 1 to 3;
o is 1 to 3;
x and y are at least 1, and
one or more methylene groups on the dithiane ring may be substituted with C$_1$-C$_4$ alkyl groups, and adjacent alkyl groups may be joined with the carbon atoms to which they are attached to form a carbocyclic ring, such as a alicyclic or aromatic ring. Preferably the dithiane ring has 8 or 9 ring atoms With respect to Formula I, it will be understood that the R$^4$ group may contain one or more catenary (in chain) organic functional groups including ester, ketone, carbonyl, amide, imide, urea, carbonate anhydride, and urethane functional groups, and further that the combinations of —X—R$^4$—, or —R$^4$—X' may in combination form a terminal functional group including imide, urea, carbonate, anhydride, and urethane functional groups. For example, where X' is —O—, and R$^4$ terminates in a carbonyl group, an ester results. Where X' is nitrogen, and R$^4$ terminates in an amide (—NHC(O)—, a urea results.

The compositions of the invention may optionally include additional monomers, typically a substituted or unsubstituted (meth)acryloyl compound, such as, for example, a di(meth)acrylate, an aliphatic (meth)acrylate having at least one functional group, and/or a (meth)acrylate with an aromatic functionality. Examples of suitable substituted (meth)acryloyl compounds include, but are not limited to phenethyl methacrylate, ethoxylated bisphenol A dimethacrylate (BisEMA6), 2-hydroxyethyl methacrylate (HEMA), bisphenol A diglycidyl dimethacrylate (bisGMA), 1,1,1-tri-[4-(methacryloxyethoxy)-phenyl]ethane (TMPE) and 1,1,1-tri-[4-(2-methyl-2-methacryloxyethoxy)-phenyl]ethane (TMMPE), urethane dimethacrylate (UDMA), triethlyene glycol dimethacrylate (TEGDMA), glycerol dimethacrylate (GDMA), ethyleneglycol dimethacrylate, neopentylglycol dimethacrylate (NPGDMA), and polyethyleneglycol dimethacrylate (PEGDMA).

The compositions of the invention also generally further comprise an initiator system, preferably a photoinitiator system containing, for example, an acylphosphine oxide photoinitiator capable of absorbing light in the range of about 300 to about 600 nm, or a multiple component photoinitiator system that may include an iodonium salt, an electron donor, and a photosensitizer.

The compositions optionally comprise one or more fillers of the sort typically used in dental materials that have been optionally treated with silanes containing free radically polymerizable functionalities.

The compositions of the invention are useful for a variety of dental treatments and restorative functions, including crown and bridge materials, fillings, adhesives, sealants, inlays, onlays, laminate veneers, luting agents or cements, denture base materials, orthodontic materials and sealants, and other dental restorative materials. The inclusion of a monomer comprising a cyclic dithiane moiety and a (meth)

acryloyl moiety in the composition results in polymerization to form a cured dental composite with low shrinkage and high mechanical properties.

The above summary is not intended to describe each embodiment or every implementation of the invention. Other embodiments, features, and advantages of the present invention will be apparent from the following detailed description thereof, and from the claims.

As used herein, a "curable" component refers to one that is capable of polymerization and/or crosslinking reactions including, for example, photopolymerization reactions and chemical polymerization techniques (e.g., ionic reactions or chemical reactions forming radicals effective to polymerize ethylenically unsaturated compounds, i.e. (meth)acrylate compounds) involving one or more compounds capable of curing. Curing reactions also include acid-base setting reactions such as those common for cement forming compositions (e.g., zinc polycarboxylate cements, glass-ionomer cements, etc.).

As used herein, "dental composition" refers to curable compositions used in the oral environment including, for example, dental adhesives, orthodontic adhesives, composites, restoratives, dental cements, orthodontic cements, sealants, coatings, impression materials, filling materials, and combinations thereof. In some embodiments, dental compositions of the present invention including a curable component can be cured to fabricate a dental article selected from the group consisting of crowns, bridges. veneers, inlays, onlays, fillings, mill blanks, impression materials, orthodontic devices, prostheses (e.g., partial or full dentures), and finishing or polishing devices as used for dental prophylaxis or restorative treatments (e.g., prophy agents such as cups, brushes, polishing agents).

As used herein, a "dental adhesive" refers to a non-filled or a lightly filled dental composition (e.g., less than 40% by weight filler), which is typically used to adhere a curable dental material (e.g., a filling material) to a tooth surface. After curing, the dental compositions are typically not tacky or sticky and therefore would not be in the class of materials known as pressure sensitive adhesives (PSAs).

As used herein:

"(meth)acryloyl"—means $CH_2=CR'C(=O)—$, where R' is H or methyl, and includes both acryloyl and methacryloyl groups;

"(meth)acryloyloxy"—means $CH_2=CR'C(=O)O—$, where R' is H or methyl;

"poly(meth)acryloyl" means a compound having two or more (meth)acryloyl groups;

"substituted (meth)acryloyl compound" is meant a (meth)acryloyl compound, such as a (meth)acrylate, having an organic substituent on the oxygen (for esters), sulfur (for thioesters) or nitrogen (for amides);

"photosensitizer" is meant any substance that either increases the rate of photo-initiated polymerization or shifts the wavelength at which polymerization occurs. Typical photosensitizers are monoketones and diketones that absorb some light within a range of 400 nm to 520 nm;

"alkyl" and "alkylene" mean the monovalent and polyvalent residues remaining after removal of one or more hydrogen atoms, respectively, from a linear or branched chain hydrocarbon having 1 to 20 carbon atoms;

"lower alkyl" means $C_1$ to $C_4$ alkyl;

"aryl" and "arylene" mean the monovalent and polyvalent residues remaining after removal of one or more hydrogen atoms, respectively, from an aromatic compound (single ring and multi- and fused-rings) having 5 to 12 ring atoms and includes substituted aromatics such as lower alkaryl and aralkyl, lower alkoxy, N,N-di(lower alkyl)amino, nitro, cyano, halo, and lower alkyl carboxylic ester, wherein "lower" means $C_1$ to $C_4$;

"cycloalkyl" and "cycloalkylene" mean the monovalent and divalent residues remaining after removal of one and two hydrogen atoms, respectively, from a cyclic hydrocarbon having 3 to 12 carbon atoms;

"curable" means that a composition may be polymerized and/or crosslinked by a variety of initiator systems, including thermal, photo and redox initiators (oxidizing/reducing agents), and combinations thereof;

"crosslinking" means the formation of a polymeric network of infinite molecular weight and occurs in polymerizations with polymeric reactants having functionalities greater than two. Additional information may be found in G. Odian, *Principles of Polymerization,* 3rd edition, 1991, John Wiley & Sons: New York, p. 108. A crosslink is formed between the pendent polymerizable functional groups by a chain growth process.

The recitation of numerical ranges by endpoints includes all numbers subsumed within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

Unless otherwise indicated, all numbers expressing quantities of ingredients, measurement of properties such as contrast ratio and so forth used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings of the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviations found in their respective testing measurements.

DETAILED DESCRIPTION

The present invention provides curable compositions comprising compounds of Formula I, that in many embodiments have low polymerization shrinkage and high mechanical properties, and that are useful in dental applications, including, for example restoratives, adhesives and primers. These compositions contain at least one monomer that comprises a cyclic dithiane moiety linked to a (meth)acryloyl moiety, as shown and described in Formula I. The composition may optionally contain additional polymerizable compounds, for example a substituted (meth)acrylate or similar compound.

In one embodiment, the compositions further include an initiator system, typically a photoinitiator system, which upon irradiation with actinic radiation of the appropriate wavelength, initiates the curing of the composition. The compositions can be cured (e.g., polymerized by conventional photopolymerization and/or chemical polymerization techniques) prior to or after applying or after the dental material. Fillers and other optional additives may also be incorporated into the composition.

The dithiane monomeric compounds may be prepared by reference to the following exemplary scheme. Here, a hydroxy functional cyclic dithiane compound is reacted with a diacid (or equivalent), then further reacted with a hydroxy functional dimethacrylate. It will be understood that the other synthetic pathways will be evident to one skilled in the art. For example, the hydroxyl of the dithiane ring compound may be replaced by another functional group, such as an amine, that is reactive toward the acid functional group of the acid. Likewise the acid group of the diacid (or equivalent) may be replaced by another functional group that is co-reactive with the hydroxyl of the cyclic dithiane compound. The diacid may be replace by another polyfunctional compound, having two or more reactive functional groups, that are co-reactive with the functional groups of the depicted cyclic dithiane compound and the depicted hydroxy functional dimethacrylate.

Exemplary combinations include hydroxyl or amino functional groups reacting with azlactone-, isocyanate-, and anhydride-functional groups and carboxyl groups reacting with isocyanate- and oxazoline-functional groups.

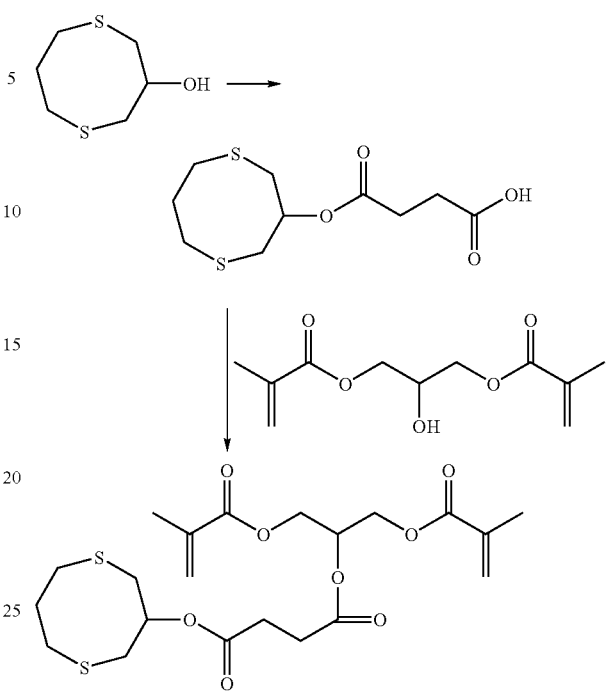

Representative examples of the compounds of the invention are as follows:

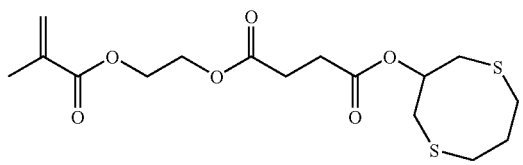
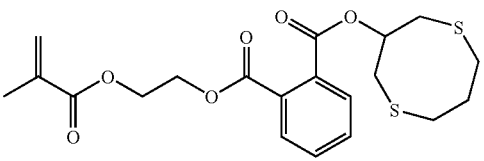
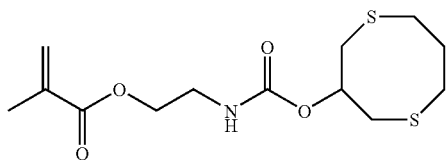
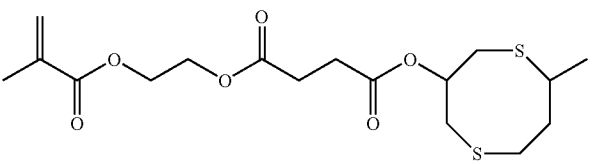
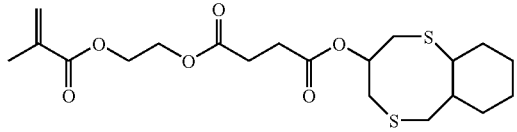
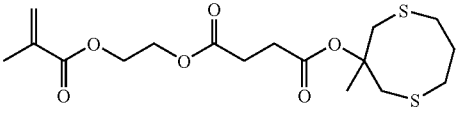
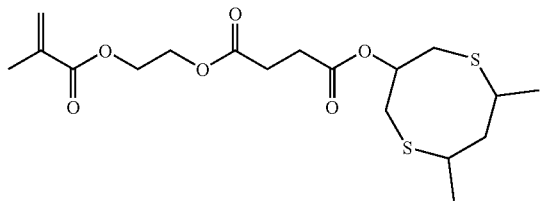
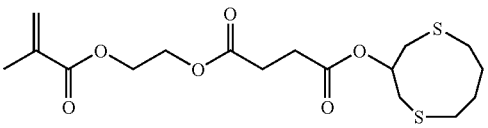

-continued
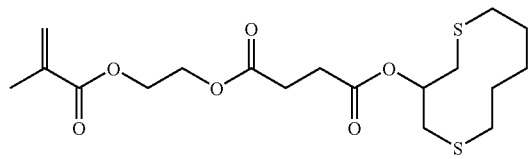
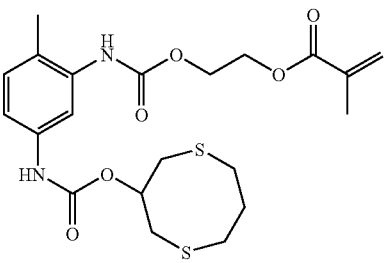
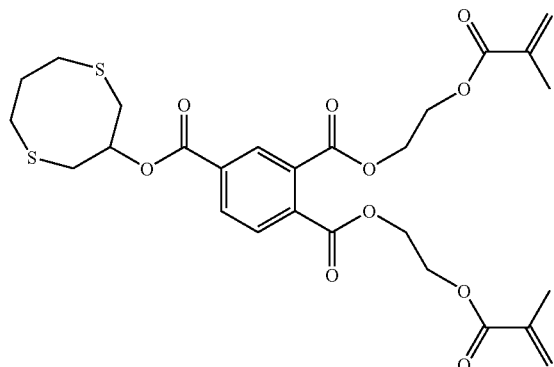
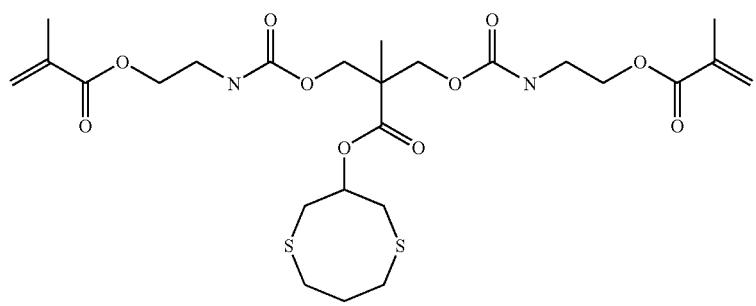
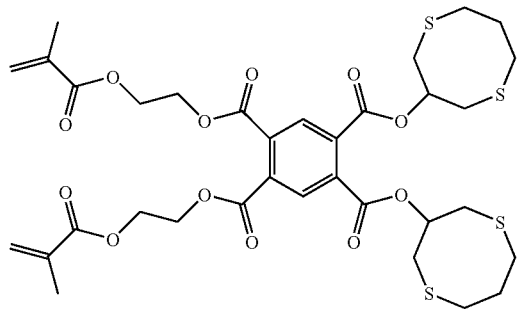
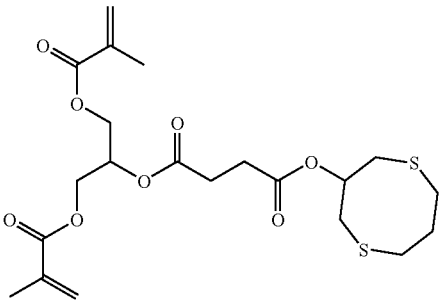
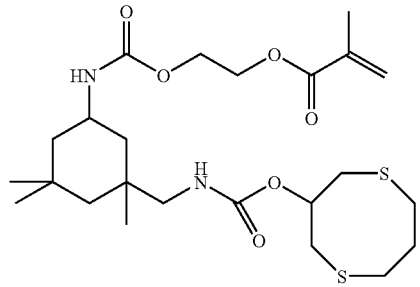
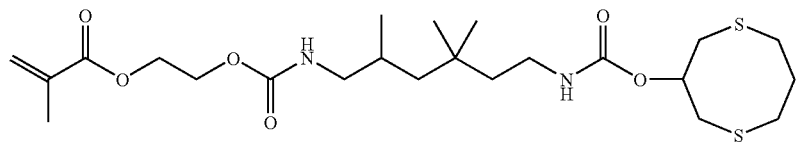

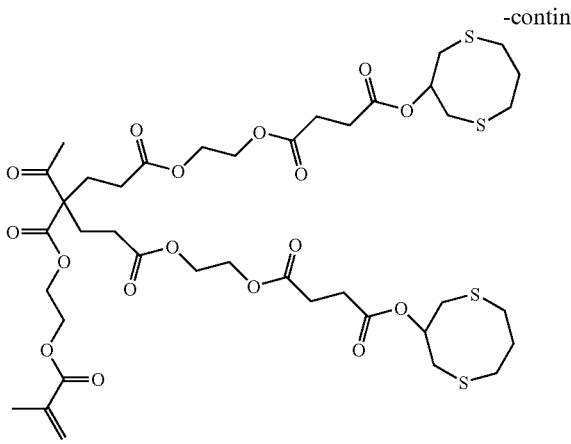
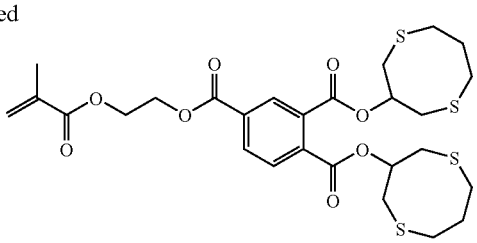

The compositions of the present invention may also include one or more ethylenically unsaturated components such as mono(meth)acryloyl compounds, in addition to the dithiane acryloyl compound. Examples of useful mono (meth)acryloyl compounds include acrylic acid esters, methacrylic acid esters, hydroxy-functional acrylic acid esters, hydroxy-functional methacrylic acid esters, acrylamides, methacrylamides, and combinations thereof.

In particular, the composition may further comprise alkyl (meth)acrylate monomers. Alkyl (meth)acrylate monomers useful in the invention include straight-chain, cyclic, and branched-chain isomers of alkyl esters containing $C_1$-$C_{30}$ alkyl groups. Due to $T_g$ and sidechain crystallinity considerations, preferred alkyl acrylate esters are those having from $C_5$-$C_{12}$ alkyl groups, although use of $C_1$-$C_4$ and $C_{13}$-$C_{14}$ alkyl groups are also useful if the combinations provide a molecule with an average number of carbon atoms between $C_5$ and $C_{12}$. However, for many applications higher, i.e. $C_{12}$-$C_{30}$ alkyl groups may be preferred. Useful specific examples of alkyl acrylate esters include: methyl acrylate, ethyl acrylate, n-propyl acrylate, 2-butyl acrylate, iso-amyl acrylate, n-hexyl acrylate, n-heptyl acrylate, isobornyl acrylate, n-octyl acrylate, iso-octyl acrylate, 2-ethylhexyl acrylate, iso-nonyl acrylate, decyl acrylate, undecyl acrylate, dodecyl acrylate, tridecyl acrylate, and tetradecyl acrylate. The corresponding methacrylates, (meth)acrylamides, and (meth)acryloyl thioesters may also be used. The curable composition may comprise 0 to 25 parts by weight of such monoacryloyl monomer units.

In addition, the curable composition of the invention may further comprise a crosslinking agent such as poly(meth)acryloyl compounds having two or more terminal (meth)acryloyl groups. Useful polyacryloyl compounds include those of the general formula:

$$R^6\text{-}(Q\text{-}C(O)\text{---}CR^1\text{=}CH_2)_z \quad (IV)$$

wherein each $R^1$ independently represents H, an alkyl group having from 1 to 4 carbon atoms; and each Q is selected from alkylene, —O—, or —$NR^1$—;

Each $R^6$ independently represents a polyvalent organic group having a valence of z, which can be cyclic, branched, or linear, aliphatic, aromatic, or heterocyclic, optionally having catenary (i.e. in chain) nitrogen, and nonperoxidic oxygen atoms, and optionally having one or more organic functional groups including ester, ketone, amide, urea, carbonate and urethane functional groups.

Each z independently represents an integer greater than or equal to 2. Preferably, z has a value of 2-6 (more preferably z has a value of 2-5, most preferably 2, or where a mixture of polyacrylates are used, z has an average value of about 2).

In one embodiment, $R^6$ may be a polyvalent organic group having a valence of at least 3. Examples of polyvalent groups $R^6$ include butylene; ethylene; propylene; 4-oxaheptalene; hexylene; and 1,4-bis(methyl)cyclohexylene.

Useful poly(meth)acryloyl compounds include, for example, (meth)acrylate monomers selected from the group consisting of (a) diacryloyl containing compounds such as ethylene glycol diacrylate, 1,3-butylene glycol diacrylate, 1,4-butanediol diacrylate, 1,6-hexanediol diacrylate, cyclohexane dimethanol diacrylate, alkoxylated hexanediol diacrylate, neopentyl glycol diacrylate, caprolactone modified neopentylglycol hydroxypivalate diacrylate, cyclohexanedimethanol diacrylate, diethylene glycol diacrylate, dipropylene glycol diacrylate, bisphenol-A diacrylate, ethoxylated bisphenol-A diacrylate, hydroxypivalaldehyde modified trimethylolpropane diacrylate, neopentyl glycol diacrylate, polyethylene glycol diacrylate, propoxylated neopentyl glycol diacrylate, tetraethylene glycol diacrylate, tricyclodecanedimethanol diacrylate, triethylene glycol diacrylate, tripropylene glycol diacrylate; (b) triacryloyl containing compounds such as glycerol triacrylate, ethoxylated triacrylates (e.g., ethoxylated trimethylolpropane triacrylate, pentaerythritol triacrylate, propoxylated triacrylates (e.g., propoxylated glyceryl triacrylate, propoxylated trimethylolpropane triacrylate, tris(2-hydroxyethyl)isocyanurate triacrylate; (c) higher functionality acryl-containing compounds such as ditrimethylolpropane tetraacrylate, dipentaerythritol pentaacrylate, ethoxylated pentaerythritol tetraacrylate, pentaerythritol tetraacrylate, caprolactone modified dipentaerythritol hexaacrylate; (d) oligomeric acryloyl compounds such as, for example, urethane acrylates, polyester acrylates, epoxy acrylates; polyacrylamide analogues of the foregoing; and combinations thereof.

Such compounds available from vendors such as, for example, Sartomer Company, Exton, Pa.; UCB Chemicals Corporation, Smyrna, Ga.; and Aldrich Chemical Company, Milwaukee, Wis. Additional useful acrylate materials include hydantoin moiety-containing polyacrylates, for example, as described in U.S. Pat. No. 4,262,072 (Wendling et al.).

Other useful poly(meth)acryloyl compounds also include, for example, free-radically polymerizable acrylate oligomers and polymers having pendant (meth)acryloyl groups wherein at least two of the (meth)acryloyl groups are acryloyl groups, including acrylated epoxies, for example, diacrylated esters of epoxy-functional materials (e.g., diacrylated esters of bisphenol A epoxy-functional material) and acrylated urethanes. Useful acrylated epoxies include, for example, acrylated epoxies available under the trade designations "EBECRYL 3500", "EBECRYL 3600", "EBECRYL 3700", and "EBECRYL 3720" from UCB Chemicals Corporation. Useful acrylated urethanes include, for example, acrylated urethanes available under the trade designations "EBECRYL 270", "EBECRYL 1290", "EBECRYL 8301", and "EBECRYL 8804" from UCB Chemicals Corporation.

With respect to the useful poly(meth)acryloyl compounds presented above, it will be understood that the corresponding methacrylates, (meth)acrylamides or (meth)acryloyl thioesters are also useful. The poly(meth)acryloyl crosslinking agent is preferably an ester of acrylic acid. It is more preferably selected from the group consisting of a difunctional ethylenically unsaturated ester of acrylic, a trifunctional ethylenically unsaturated ester of acrylic, a tetrafunctional ethylenically unsaturated ester of acrylic, and a combination thereof. Of these, difunctional and trifunctional ethylenically unsaturated esters of acrylic acid are more preferred.

Typically, compositions of the present invention include at least 5% by weight, more typically at least 10% by weight, and most typically at least 15% by weight dithiane monomers, based on the total weight of the unfilled (without filler) composition. Typically, compositions of the present invention include at most 95% by weight, more typically at most 90% by weight, and most typically at most 80% by weight dithiane monomers, based on the total weight of the unfilled composition.

More specifically, the compositions may comprise up to 100 wt. % dithiane monomer of Formula I, preferably 5 to 75 wt. % and more preferably 5 to 35 wt. %. The composition may further comprise up to 20 wt. % other monoacryloyl compounds, generally 1 to 10 wt. %, and up to 95 wt. % polyacryloyl crosslinking agent, generally 65 to 95 wt. %, based on the total weight of the unfilled composition.

The invention further provides dental etchant and primer compositions that include one or more ethylenically unsaturated compounds with acid functionality in addition to the previously described monomers (acid functional monomers). As used herein, acid functional monomers are meant to include monomers and oligomers having ethylenic unsaturation and acid and/or acid-precursor functionality. Acid-precursor functionalities include, for example, anhydrides, acid halides, and pyrophosphates. The acid functionality can include oxyacids of C, B, P or S or combinations thereof. Examples include carboxylic acid functionality, phosphoric acid functionality, phosphonic acid functionality, sulfonic acid functionality, or combinations thereof.

Acid functional monomers include, for example, α,β-unsaturated acidic compounds such as glycerol phosphate mono (meth)acrylates, glycerol phosphate di(meth)acrylates, hydroxyethyl (meth)acrylate (e.g., HEMA) phosphates, bis((meth)acryloyloxyethyl) phosphate, ((meth)acryloyloxypropyl)phosphate, bis((meth)acryloyloxypropyl)phosphate, bis((meth)acryloyloxy)propyloxy phosphate, (meth)acryloyloxyhexyl phosphate, bis((meth)acryloyloxyhexyl) phosphate, (meth)acryloyloxyoctyl phosphate, bis((meth)acryloyloxyoctyl)phosphate, (meth)acryloyloxydecyl phosphate, bis((meth)acryloyloxydecyl)phosphate, caprolactone methacrylate phosphate, citric acid di- or tri-methacrylates, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like, may be used as components in the curable component system. Also monomers, oligomers, and polymers of unsaturated carbonic acids such as (meth)acrylic acids, aromatic (meth)acrylated acids (e.g., methacrylated trimellitic acids), and anhydrides thereof can be used. Certain preferred compositions of the present invention include acid functional monomers having at least one P—OH moiety.

Certain of these compounds are obtained, for example, as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. Mixtures of such compounds can be used if desired.

Additional acid functional monomers include, for example, polymerizable bisphosphonic acids as disclosed for example, in U.S. Pat. Publication No. 2004/0206932 (Abuelyaman et al.); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and European Pat. Application Publication Nos. EP 712,622 (Tokuyama Corp.) and EP 1,051,961 (Kuraray Co., Ltd.).

Compositions of the present invention can also include compositions that include combinations of acid functional monomers. Typically the compositions are self-adhesive and are non-aqueous. For example, such compositions can include: a first compound including at least one (meth)acryloyl group and at least one —O—P(O)(OH)$_x$ group, wherein x=1 or 2, and wherein the at least one —O—P(O)(OH)$_x$ group and the at least one (meth)acryloyl group are linked together by a $C_1$-$C_4$ hydrocarbon group; a second compound including at least one (meth)acryloxy group and at least one —O—P(O)(OH)$_x$ group, wherein x=1 or 2, and wherein the at least one —O—P(O)(OH)$_x$ group and the at least one (meth)acryloxy group are linked together by a $C_5$-$C_{12}$ hydrocarbon group; an ethylenically unsaturated compound without acid functionality; an initiator system; and a filler. Such compositions are described, for example, in U.S. Published Application 2007-0248927 (Luchterhandt et al.).

Typically, the etchant compositions of the present invention include at least 1% by weight, more typically at least 3% by weight, and most typically at least 5% by weight acid functional monomers, based on the total weight of the unfilled composition. Typically, compositions of the present invention include at most 80% by weight, more typically at most 70% by weight, and most typically at most 60% by weight acid functional monomers, based on the total weight of the unfilled composition.

In one embodiment, the etchant compositions may comprise:
at least 5 wt. % dithiane monomers;
10 to 75 wt. %, preferably 50 to 75 wt. % acid functional monomers,
1 to 20 wt. % polyacryloyl crosslinking agent; and
less than 10 wt. % monoacryloyl monomers.

The compositions of the present invention can also contain fillers. Fillers may be selected from one or more of a wide variety of materials suitable for incorporation in compositions used for dental applications, such as fillers currently used in dental restorative compositions, and the like.

The filler is preferably finely divided. The filler can have a unimodial or polymodial (e.g., bimodal) particle size distribution. Typically, the maximum particle size (the largest dimension of a particle, typically, the diameter) of the filler is less than 20 micrometers, more typically less than 10 micrometers, and most typically less than 5 micrometers. Typically, the average particle size of the filler is less than 0.4 micrometers, more typically less than 0.1 micrometers, and most typically less than 0.075 micrometer.

The filler can be an inorganic material. It can also be a crosslinked organic material that is insoluble in the resin system (i.e., the curable components), and is optionally filled with inorganic filler. The filler should in any event be nontoxic and suitable for use in the mouth. The filler can be radiopaque or radiolucent. The filler typically is substantially insoluble in water.

Examples of suitable inorganic fillers are naturally occurring or synthetic materials including, but not limited to: quartz (i.e., silica, $SiO_2$); nitrides (e.g., silicon nitride); glasses and fillers derived from, for example, Zr, Sr, Ce, Sb, Sn, Ba, Zn, and Al; feldspar; borosilicate glass; kaolin; talc; zirconia; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles are quartz (i.e., silica), submicron silica, zirconia, submicron zirconia, and non-vitreous microparticles of the type described in U.S. Pat. No. 4,503,169 (Randklev). Mixtures of these non-acid-reactive fillers are also contemplated, as well as combination fillers made from organic and inorganic materials.

The filler can also be an acid-reactive filler. Suitable acid-reactive fillers include metal oxides, glasses, and metal salts. Typical metal oxides include barium oxide, calcium oxide, magnesium oxide, and zinc oxide. Typical glasses include borate glasses, phosphate glasses, and fluoroaluminosilicate ("FAS") glasses. FAS glasses are particularly preferred. The FAS glass typically contains sufficient elutable cations so that a cured dental composition will form when the glass is mixed with the components of the curable composition. The glass also typically contains sufficient elutable fluoride ions so that the cured composition will have cariostatic properties. The glass can be made from a melt containing fluoride, alumina, and other glass-forming ingredients using techniques familiar to those skilled in the FAS glassmaking art. The FAS glass typically is in the form of particles that are sufficiently finely divided so that they can conveniently be mixed with the other cement components and will perform well when the resulting mixture is used in the mouth.

Generally, the average particle size (typically, diameter) for the FAS glass is no greater than 12 micrometers, typically no greater than 10 micrometers, and more typically no greater than 5 micrometers as measured using, for example, a sedimentation analyzer. Suitable FAS glasses will be familiar to those skilled in the art, and are available from a wide variety of commercial sources, and many are found in currently available glass ionomer cements such as those commercially available under the trade designations VITREMER, VITREBOND, RELY X LUTING CEMENT, RELY X LUTING PLUS CEMENT, PHOTAC-FIL QUICK, KETAC-MOLAR, and KETAC-FIL PLUS (3M ESPE Dental Products, St. Paul, Minn.), FUJI II LC and FUJI IX (G-C Dental Industrial Corp., Tokyo, Japan) and CHEMFIL Superior (Dentsply International, York, Pa.). Mixtures of fillers can be used if desired.

The surface of the filler particles can also be treated with a coupling agent in order to enhance the bond between the filler and the resin. Any coupling agent with a group that is co-polymerizable with the monomers of this invention would be suitable. The coupling agent could optionally contain a cyclic allylic sulfide unit. The use of suitable coupling agents include γ-methacryloxypropyltrimethoxysilane, gamma-mercaptopropyltriethoxysilane, gamma-aminopropyltrimethoxysilane, and the like. Silane-treated zirconia-silica ($ZrO_2$—$SiO_2$) filler, silane-treated silica filler, silane-treated zirconia filler, and combinations thereof are especially preferred in certain embodiments.

Other suitable fillers are disclosed in U.S. Pat. No. 6,387,981 (Zhang et al.) and U.S. Pat. No. 6,572,693 (Wu et al.) as well as U.S. Pat. No. 6,387,981 (Zhang et al.), WO 01/30306 (Windisch et al.), U.S. Pat. No. 6,899,948 (Zhang et al.), and U.S. Pat. No. 7,393,882 (Wu et al.). Filler components described in these references include non-aggregated nano-sized silica particles, non-aggregated nanosized metal oxide particles, clusters of nanosized particles, and combinations thereof. Nanofillers are also described in U.S. Pat. No. 7,156,911 (Kangas et al.); U.S. published application 2005/0256223 (Kolb et al.); U.S. Pat. No. 7,090,821 (Craig et al.); and U.S. Pat. No. 7,090,722 (Budd et al.). These references, in summary, describe the following nanofiller containing compositions: U.S. Pat. No. 7,156,911 (Kangas et al.) describes stable ionomer compositions (e.g., glass ionomer) containing nanofillers that provide the compositions with improved properties over previous ionomer compositions. In one embodiment, the composition is a curable dental composition comprising a polyacid (e.g., a polymer having a plurality of acidic repeating groups); an acid-reactive filler; at least 10 percent by weight nanofiller or a combination of nanofillers each having an average particle size no more than 200 nanometers; water; and optionally a polymerizable component (e.g., an ethylenically unsaturated compound, optionally with acid functionality).

U.S. published application 2005/0256223 (Kolb et al.) describes stable ionomer (e.g., glass ionomer) compositions containing nanozirconia fillers that provide the compositions with improved properties, such as ionomer systems that are optically translucent and radiopaque. The nanozirconia is surface modified with silanes to aid in the incorporation of the nanozirconia into ionomer compositions, which generally contain a polyacid that might otherwise interact with the nanozirconia causing coagulation or aggregation resulting in undesired visual opacity. In one aspect, the composition can be a curable dental composition including a polyacid; an acid-reactive filler; a nanozirconia filler having a plurality of silane-containing molecules attached onto the outer surface of the zirconia particles; water; and optionally a polymerizable component (e.g., an ethylenically unsaturated compound, optionally with acid functionality).

U.S. Pat. No. 7,090,721 (Craig et al.) describes stable ionomer compositions (e.g., glass ionomers) containing nanofillers that provide the compositions with enhanced optical translucency. In one embodiment, the composition is a curable dental composition including a polyacid (e.g., a polymer having a plurality of acidic repeating groups); an acid-reactive filler; a nanofiller; an optional polymerizable component (e.g., an ethylenically unsaturated compound, optionally with acid functionality); and water. The refractive index of the combined mixture (measured in the cured state or the uncured state) of the polyacid, nanofiller, water and optional polymerizable component is generally within 4 percent of the refractive index of the acid-reactive filler, typically within 3 percent thereof, more typically within 1 percent thereof, and even more typically within 0.5 percent thereof.

U.S. Pat. No. 7,090,722 (Budd et al.) describes dental compositions that can include an acid-reactive nanofiller (i.e., a nanostructured filler) and a curable resin (e.g., a polymerizable ethylenically unsaturated compound. The acid-reactive nanofiller can include an oxyfluoride material that is acid-reactive, non-fused, and includes a trivalent metal (e.g., alumina), oxygen, fluorine, an alkaline earth metal, and optionally silicon and/or a heavy metal.

For some embodiments of the present invention that include filler (e.g., dental adhesive compositions), the compositions preferably include at least 1% by weight, more preferably at least 2% by weight, and most preferably at least 5% by weight filler, based on the total weight of the composition. For such embodiments, compositions of the present invention preferably include at most 40% by weight, more preferably at most 20% by weight, and most preferably at most 15% by weight filler, based on the total weight of the composition. Thus the dental adhesive composition may comprise 1 to 40 wt. % filler and 99 to 60 wt. % curable composition (monomers and crosslinking agents).

For other embodiments (e.g., where the composition is a dental restorative or an orthodontic adhesive), compositions of the present invention preferably include at least 40% by weight, more preferably at least 45% by weight, and most preferably at least 50% by weight filler, based on the total weight of the composition. For such embodiments, compositions of the present invention preferably include at most 90% by weight, more preferably at most 80% by weight, even more preferably at most 70% by weight filler, and most preferably at most 50% by weight filler, based on the total weight of the composition. Thus the dental adhesive composition may comprise 40 to 90 wt. % filler and 60 to 10 wt. % curable composition (monomers and crosslinking agents).

Optionally, compositions of the present invention may contain solvents (e.g., alcohols (e.g., propanol, ethanol), ketones (e.g., acetone, methyl ethyl ketone), esters (e.g., ethyl acetate), other nonaqueous solvents (e.g., dimethylformamide, dimethylacetamide, dimethylsulfoxide, 1-methyl-2-pyrrolidinone)), and water.

If desired, the compositions of the invention can contain additives such as indicators, dyes, pigments, inhibitors, accelerators, viscosity modifiers, wetting agents, buffering agents, stabilizers, and other similar ingredients that will be apparent to those skilled in the art. Viscosity modifiers include the thermally responsive viscosity modifiers (such as PLURONIC F-127 and F-108 available from BASF Wyandotte Corporation, Parsippany, N.J.) and may optionally include a polymerizable moiety on the modifier or a polymerizable component different than the modifier. Such thermally responsive viscosity modifiers are described in U.S. Pat. No. U.S. Pat. No. 6,669,927 (Trom et al.) and U.S. Pat. Publication No. 2004/0151691 (Oxman et al.).

Additionally, medicaments or other therapeutic substances can be optionally added to the dental compositions. Examples include, but are not limited to, fluoride sources, whitening agents, anticaries agents (e.g., xylitol), calcium sources, phosphorus sources, remineralizing agents (e.g., calcium phosphate compounds), enzymes, breath fresheners, anesthetics, clotting agents, acid neutralizers, chemotherapeutic agents, immune response modifiers, thixotropes, polyols, anti-inflammatory agents, antimicrobial agents (in addition to the antimicrobial lipid component), antifungal agents, agents for treating xerostomia, desensitizers, and the like, of the type often used in dental compositions. Combination of any of the above additives may also be employed. The selection and amount of any one such additive can be selected by one of skill in the art to accomplish the desired result without undue experimentation.

In certain embodiments, the compositions of the present invention are photopolymerizable, i.e., the compositions contain a photopolymerizable component and a photoinitiator (i.e., a photoinitiator system) that upon irradiation with actinic radiation initiates the free radical polymerization (or curing) of the composition.

Suitable photoinitiators for polymerizing free radically photopolymerizable compositions include the class of phosphine oxides that typically have a functional wavelength range of 300 nm to 1200 nm, more typically in the range of 300 nm to 600 nm. Especially useful phosphine oxide free radical initiators, which generally have a functional wavelength range of 380 nm to 450 nm, are acyl and bisacyl phosphine oxides such as those described in U.S. Pat. No. 4,298,738 (Lechtken et al.), U.S. Pat. No. 4,324,744 (Lechtken et al.), U.S. Pat. No. 4,385,109 (Lechtken et al.), U.S. Pat. No. 4,710,523 (Lechtken et al.), and U.S. Pat. No. 4,737,593 (Ellrich et al.), U.S. Pat. No. 6,251,963 (Kohler et al.); and EP Application No. 0 173 567 A2 (Ying).

Commercially available phosphine oxide photoinitiators capable of free-radical initiation when irradiated at wavelength ranges of greater than 380 nm to 450 nm include bis(2,4,6-trimethylbenzoyl)phenyl phosphine oxide (IRGACURE 819, Ciba Specialty Chemicals, Tarrytown, N.Y.), bis (2,6-dimethoxybenzoyl)-(2,4,4-trimethylpentyl) phosphine oxide (CGI 403, Ciba Specialty Chemicals), a 25:75 mixture, by weight, of bis(2,6-dimethoxybenzoyl)-2,4,4-trimethylpentyl phosphine oxide and 2-hydroxy-2-methyl-1-phenyl-propan-1-one (IRGACURE 1700, Ciba Specialty Chemicals), bis(.eta.5-2-4-cyclopentadien-1-yl)-bis(2,6-difluoro-3-(1H-pyrrol-1yl)-phenyl)titanium (IRGACURE 784, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR 4265, Ciba Specialty Chemicals), and ethyl 2,4,6-trimethylbenzylphenyl phosphinate (LUCIRIN LR8893X, BASF Corp., Charlotte, N.C.).

Other suitable photoinitiators (i.e., photoinitiator systems that include one or more compounds) for polymerizing free radically photopolymerizable compositions include binary and tertiary systems. Typical tertiary photoinitiator systems include an iodonium salt, a photosensitizer, and an electron donor compound as described in U.S. Pat. No. 5,545,676 (Palazzotto et al.). Preferred iodonium salts are the diaryl iodonium salts, e.g., diphenyliodonium chloride, diphenyliodonium hexafluorophosphate, diphenyliodonium tetrafluoroborate, and tolylcumyliodonium tetrakis(pentafluorophenyl)borate. Preferred photosensitizers are monoketones and diketones that absorb some light within a range of 400 nm to 520 nm (preferably, 450 nm to 500 nm). More preferred compounds are alpha diketones that have some light absorption within a range of 400 nm to 520 nm (even more preferably, 450 to 500 nm). Preferred compounds are camphorquinone, benzil, furil, 3,3,6,6-tetramethylcyclohexanedione, phenanthraquinone, 1-phenyl-1,2-propanedione and other 1-aryl-2-alkyl-1,2-ethanediones, and cyclic alpha diketones. Most preferred is camphorquinone. Preferred electron donor compounds include substituted amines, e.g., ethyl dimethylaminobenzoate. Other suitable tertiary photoinitiator systems useful for photopolymerizing cationically polymerizable resins are described, for example, in U.S. Pat. No. 6,765,036 (Dede et al.).

Illustrative tertiary amines useful in the invention include ethyl 4-(N,N-dimethylamino)benzoate and N,N-dimethylaminoethyl methacrylate. When present, the amine reducing agent is present in the photopolymerizable composition in an amount from 0.1 weight percent to 5.0 weight percent, based on the total weight of the composition. Useful amounts of other initiators are well known to those of skill in the art.

The compositions of the invention typically contain at least 0.04 wt-%, more typically at least 0.08 wt-%, even more typically at least 0.12 wt-%, and most typically at least 0.18 wt-% of a photosensitizer, based on the total weight of the composition.

The photoinitiator system is present in an amount sufficient to provide the desired rate of curing (e.g., polymerizing and/or crosslinking). The amounts of photoinitiator system components in a composition will be dependent in part on the light source, the thickness of the layer to be exposed to radiant energy, and the extinction coefficient of the component(s).

While not wishing to be bound by theory, it is believed that electron transfer to the dithiane ring competes with electron transfer to the tertiary amine (of tertiary photoinitiator systems), resulting in a retardation of the rate of (meth)acryloyl polymerization. This retardation improves the shrinkage observed during curing.

In some embodiments, the compositions of the present invention are chemically curable, i.e. the compositions contain a chemically curable component and a chemical initiator (i.e., initiator system) that can polymerize, cure, or otherwise cure the composition without dependence on irradiation with actinic radiation. Such chemically curable compositions are sometimes referred to as "self-cure" compositions and may include glass ionomer cements, resin-modified glass ionomer cements, redox cure systems, and combinations thereof.

The chemically curable compositions may include redox cure systems that include a curable component (e.g., an ethylenically unsaturated polymerizable component) and redox agents that include an oxidizing agent and a reducing agent. Suitable curable components, redox agents, optional acid-functional components, and optional fillers that are useful in the present invention are described in U.S. Pat. No. 5,154,762 (Mitra et al.), and U.S. Pat. No. 7,073,074 (Mitra et al.) and U.S. Pat. No. 6,982,288 (Mitra et al.).

The reducing and oxidizing agents should react with or otherwise cooperate with one another to produce free-radicals capable of initiating polymerization of the resin system (e.g., the ethylenically unsaturated component). This type of cure is a dark reaction, that is, it is not dependent on the presence of light and can proceed in the absence of light. The reducing and oxidizing agents are preferably sufficiently shelf-stable and free of undesirable colorization to permit their storage and use under typical dental conditions. They should be sufficiently miscible with the resin system (and preferably water-soluble) to permit ready dissolution in (and discourage separation from) the other components of the curable composition.

Useful reducing agents include ascorbic acid, ascorbic acid derivatives, and metal complexed ascorbic acid compounds as described in U.S. Pat. No. 5,501,727 (Wang et al.); amines, especially tertiary amines, such as 4-tert-butyl dimethylaniline and N,N-bis(hydroxyethyl)-p-toluidine; aromatic sulfinic salts, such as p-toluenesulfinic salts and benzenesulfinic salts; thioureas, such as 1-ethyl-2-thiourea, tetraethyl thiourea, tetramethyl thiourea, 1,1-dibutyl thiourea, and 1,3-dibutyl thiourea; and mixtures thereof. Other secondary reducing agents may include cobalt (II) chloride, ferrous chloride, ferrous sulfate, hydrazine, hydroxylamine (depending on the choice of oxidizing agent), salts of a dithionite or sulfite anion, and mixtures thereof. Preferably, the reducing agent is an amine.

Suitable oxidizing agents will also be familiar to those skilled in the art, and include but are not limited to persulfuric acid and salts thereof, such as sodium, potassium, ammonium, cesium, and alkyl ammonium salts. Additional oxidizing agents include peroxides such as benzoyl peroxides, hydroperoxides such as cumyl hydroperoxide, t-butyl hydroperoxide, and amyl hydroperoxide, as well as salts of transition metals such as cobalt (III) chloride and ferric chloride, cerium (IV) sulfate, perboric acid and salts thereof, permanganic acid and salts thereof, perphosphoric acid and salts thereof, and mixtures thereof.

It may be desirable to use more than one oxidizing agent or more than one reducing agent. Small quantities of transition metal compounds may also be added to accelerate the rate of redox cure. In some embodiments it may be preferred to include a secondary ionic salt to enhance the stability of the polymerizable composition as described in U.S. Pat. No. 6,982,288 (Mitra et al.).

The reducing and oxidizing agents are present in amounts sufficient to permit an adequate free-radical reaction rate. This rate may be evaluated by combining all of the ingredients of the curable composition except for the optional filler, and observing whether or not a cured mass is obtained.

Typically, the reducing agent is present in an amount of at least 0.01% by weight, and more typically at least 0.1% by weight, based on the total weight (including water) of the components of the curable composition. Typically, the reducing agent is present in an amount of no greater than 10% by weight, and more typically no greater than 5% by weight, based on the total weight (including water) of the components of the curable composition.

Typically, the oxidizing agent is present in an amount of at least 0.01% by weight, and typically at least 0.10% by weight, based on the total weight (including water) of the components of the curable composition. Typically, the oxidizing agent is present in an amount of no greater than 10% by weight, and more typically no greater than 5% by weight, based on the total weight (including water) of the components of the curable composition.

The reducing or oxidizing agents can be microencapsulated as described in U.S. Pat. No. 5,154,762 (Mitra et al.). This will generally enhance shelf stability of the curable composition, and if necessary permit packaging the reducing and oxidizing agents together. For example, through appropriate selection of an encapsulant, the oxidizing and reducing agents can be combined with an acid-functional component and optional filler and kept in a storage-stable state. A redox cure system can be combined with other cure systems, e.g., with a curable composition such as described U.S. Pat. No. 5,154,762 (Mitra et al.).

The photocurable compositions of the present invention can be prepared by combining the dithiane monomer (having at least one cyclic dithiane moiety and at least one (meth)acryloyl moiety) with other optional components, such as one or more additional monomers, e.g., an ethylenically unsaturated component (e.g., a substituted (meth)acryloylcompound), using conventional mixing techniques. The resulting composition may optionally contain enhancers, surfactants, fillers, water, co-solvents, and other additives as described herein. In use, the compositions may contain a photoinitiator system and be cured by photoinitiation, or may be cured by chemical polymerization and contain a redox cure system in which the composition contains an oxidizing agent and a reducing agent. Alternatively, the curable composition may contain different initiator systems, such that the composition can be both a photopolymerizable and a chemically polymerizable composition.

The curable compositions of the invention can be supplied in a variety of forms including one-part systems and multi-part systems, e.g., two-part powder/liquid, paste/liquid, and paste/paste systems. Other forms employing multi-part combinations (i.e., combinations of two or more parts), each of which is in the form of a powder, liquid, gel, or paste is also possible. In a redox multi-part system, one part typically contains the oxidizing agent and another part typically contains the reducing agent. In multi-part systems containing an antimicrobial lipid component, one part typically contains the antimicrobial lipid component and another part contains either the curable component or other components of the final composition. The components of the curable composition can be included in a kit, where the contents of the composition are packaged to allow for storage of the components until they are needed.

When used as a dental composition, the components of the curable compositions can be mixed and clinically applied using conventional techniques. A curing light is generally required for the initiation of photopolymerizable compositions. The compositions can be in the form of composites or restoratives that adhere very well to dentin and/or enamel. Optionally, a primer layer can be used on the tooth tissue on which the curable composition is used. The compositions, e.g., containing a FAS glass or other fluoride releasing material, can also provide very good long-term fluoride release. Some embodiments of the invention may provide glass ionomer cements or adhesives that can be cured in bulk without the application of light or other external curing energy, do not require a pre-treatment, have improved physical properties.

The compositions of the invention are particularly well adapted for use in the form of a wide variety of dental materials, which may be filled or unfilled. They can be used in sealants, coatings, or dental adhesives, which are lightly filled composites (up to 40 wt-% filler, based on the total weight of the composition) or unfilled compositions that are cured after being dispensed adjacent to a tooth (i.e., placing a dental material in temporary or permanent bonding or touching contact with a tooth). They can be used in dental and orthodontic cements, orthodontic adhesives, composites, filling materials, impression materials, and restoratives, which are typically filled compositions (preferably containing greater than 40 wt-% filler and up to 90 wt-% filler).

The compositions can also be used in prostheses that are shaped and polymerized for final use (e.g., as a crown, bridge, veneer, inlay, onlay, or the like), before being disposed adjacent to a tooth. Such preformed articles can be ground or otherwise formed into a custom-fitted shape by the dentist or other user. Although the cured dental material can be any of a wide variety of materials that are prepared from curable components, preferably, the cured dental material is not a surface pre-treatment material (e.g., etchant or primer). Rather, preferably, the cured dental material is a restorative (e.g., filling or prosthesis), mill blank, or orthodontic device.

The compositions have utility in clinical applications where cure of conventional light-curable cement may be difficult to achieve. Such applications include, but are not limited to, deep restorations, large crown build-ups, endodontic restorations, attachment of orthodontic brackets (including pre-coated brackets, where, for example, a paste portion could be pre-applied to the bracket and a liquid portion could later be brushed onto a tooth), bands, buccal tubes, and other devices, luting of metallic crowns or other light-impermeable prosthetic devices to teeth, and other restorative applications in inaccessible areas of the mouth.

Typical compositions are used as dental adhesives, orthodontic adhesives, composites, restoratives, dental cements, orthodontic cements, sealants, coatings, impression materials, filling materials, or combinations thereof.

Further features and advantages of this invention are further illustrated by the following examples, which are in no way intended to be limiting thereof. The present invention should not be considered limited to the particular examples described herein, but rather should be understood to cover all aspects of the invention as fairly set out in the attached claims. Various modifications, equivalent processes, as well as numerous structures to which the present invention can be applicable will be readily apparent to those of skill in the art to which the present invention is directed upon review of the instant specification.

Unless otherwise indicated, all parts and percentages provided in the examples are on a weight basis, all water is deionized water, and all molecular weights are weight average molecular weight.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Test Methods

Watts Shrinkage Test Method

The Watts Shrinkage (Watts) Test Method measures shrinkage of a test sample in terms of volumetric change after curing. The sample preparation (90-mg uncured composite test sample) and test procedure were carried out as described in the following reference: Determination of Polymerization Shrinkage Kinetics in Visible-Light-Cured Materials: Methods Development, Dental Materials, October 1991, pages 281-286. Results in terms of percent shrinkage were reported as the average of three replicates for each sample.

Barcol Hardness Test Method

Barcol Hardness of a test sample was measured according to the following procedure. An uncured composite sample was cured in 2.5-mm thick TEFLON mold sandwiched between a sheet of polyester (PET) film and a glass slide for 30 seconds with an ELIPAR Freelight 2 dental curing light (3M Company). After irradiation, the PET film was removed and the hardness of the sample at both the top and the bottom of the mold was measured using a Barber-Coleman Impressor (a hand-held portable hardness tester; Model GYZJ 934-1; Barber-Coleman Company, Industrial Instruments Division, Lovas Park, Ind.) equipped with an indenter. Top and bottom Barcol Hardness values were measured at 5 minutes after light exposure.

Table of Abbreviations

| Abbreviation or Trade Designation | Description |
|---|---|
| C-8 alcohol | 3-Hydroxy-1,5-dithiacyclooctane was prepared according to the Preparatory Example 1 described herein. |
| BisGMA | 2,2-bis[4-(2-hydroxy-3-methacryloyloxypropoxy)phenyl]propane |
| TEGDMA | Triethylene glycol dimethacrylate commercially available from Sartomer; Exton, PA. |
| UDMA | Diurethane dimethacrylate (CAS No. 41137-60-4), commercially available as Rohamere 6661-0 commercially available from Rohm Tech, Inc.; Malden, MA. |
| BisEMA-6 | Ethoxylated bisphenol A dimethacrylate commercially available from Sartomer; Exton, PA. |
| CPQ | Camphorquinone |
| EDMAB | Ethyl 4-(N,N-dimethylamino)benzoate |
| DPIHFP | Diphenyl Iodonium Hexafluorophosphate commercially available from Alpha Aesar; Ward Hill, MA. |
| Filler A | Silane-treated, nano-sized silica and zirconia particles loosely aggregated as substantially amorphous clusters were prepared in the form of a dry powder according to the procedure for Filler B in U.S. Pat. Publication No. 2003/0181541 (Wu et al.). |
| DMAP | 4-(N,N-Dimethylamino)pyridine |
| DCC | N,N-Dicyclohexyl carbodiimide commercially available from Alpha Aesar; Ward Hill, MA. |

Preparatory Example 1

3-Hydroxy-1,5-dithiacyclooctane

A first solution of 1,3-propanedithiol (10.82 grams, 0.10 moles, commercially available from Alfa Aesar; Ward Hill, Mass.) and ethanol (45 milliliters) was placed in a 60-milliliter syringe. A second solution of epichlorohydrin (9.25 grams, 0.10 moles) and ethanol (45 milliliters) was placed in a second 60-milliliter syringe. Both solutions were slowly added dropwise to a mixture of sodium hydroxide (8.80 grams, 0.22 moles) and ethanol (250 milliliters) at room temperature over 10 hours. After stirring for an additional 8 hours, the reaction mixture was concentrated under vacuum, and then diluted with ethyl acetate (200 milliliters). The organic phase was washed with water (200 milliliters) and saturated sodium chloride in water (100 milliliters) and dried over magnesium sulfate. The solvent was removed under reduced pressure to give the crude product that was purified by column chromatography over silica gel using a mixture of ethyl acetate in hexane (30/70 parts by weight). The product was isolated as an oil. (6.99 grams, 43% yield).

Example 1

1-(2-Methacryloyloxyethyl)-2-(1,5-dithiacyclooctan-3-yl) Succinate

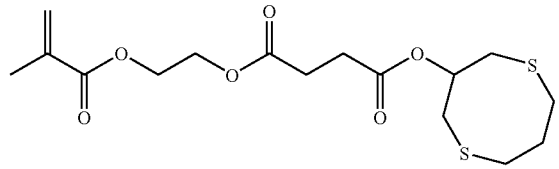

mono-2-Methacryloyloxyethyl succinate (4.20 grams, 18 millimoles) and 3-hydroxy-1,5-dithiacyclooctane (3.00 grams, 18 millimoles) were dissolved in methylene chloride (50 milliliters) in a 3-neck flask equipped with a magnetic stirring bar and nitrogen gas inlet. DMAP (0.22 grams, 2 millimoles) was added and the resulting mixture was cooled in an ice bath for 20 minutes. To the cooled solution was added DCC (4.14 grams, 20 millimoles). The resulting mixture was then stirred in the ice bath for 2 hours and room temperature for 16 hours. The resulting precipitate was removed by vacuum filtration. The filtrate was then washed once with saturated sodium bicarbonate (50 milliliters), and once with saturated sodium chloride in water (50 milliliters). After drying over magnesium sulfate, the solvent was removed under reduced pressure. The crude oil was purified by column chromatography over silica gel using a mixture of ethyl acetate in hexane (30/70 parts by weight). The product was isolated as an oil. (5.72 grams, 83% yield). Purity and structure of Example 1 were confirmed by $^1$H NMR.

Example 2

1-(2-Methacryloyloxyethyl)-2-(1,5-dithiaoctan-3-yl) Phthalate

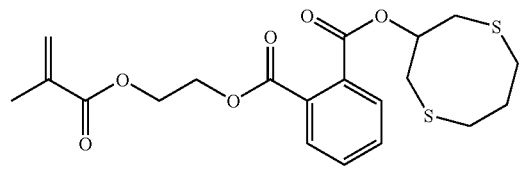

Example 2 was prepared following the general procedure of esterification described for Example 1 using 3-hydroxy-1,5-dithiacyclooctane and mono-2-Methacryloyloxyethyl phthalate. Purity and structure verification of Example 2 were confirmed by $^1$H NMR.

Comparative Example C1

(2-Methacryloyloxyethyl)-2-(cyclooctyl) Succinate

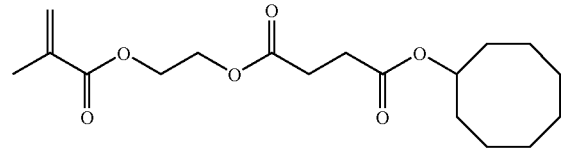

mono-2-Methacryloyloxyethyl succinate (8.35 grams, 36 millimoles) and cyclooctanol (4.65 grams, 36 millimoles) were dissolved in methylene chloride (200 milliliters) in a 3-neck flask equipped with a magnetic stirring bar and nitrogen gas inlet. DMAP (0.44 gram, 4 millimoles) was added and the resulting mixture was cooled in an ice bath for 20 minutes. To the cooled solution was added DCC (7.84 grams, 38 millimoles). The resulting mixture was then stirred in the ice bath for 2 hours and then at room temperature for 48 hours. The resulting precipitate was removed by vacuum filtration. The solvent was then removed under reduced pressure and the crude product was purified by column chromatography over silica gel using a mixture of ethyl acetate/hexane (15/85). The product was isolated as an oil. (10.99 grams, 89% yield). Purity and structure of Comparative Example 1 were confirmed by ¹H NMR.

Examples 3-8 and Comparative Examples C2-C4

Dental compositions containing one or more methacrylate monomer and C-8 alcohol derivatives were prepared as follows: The photoinitiator components (e.g., CPQ, EDMAB, and DPIHFP), methacrylate monomers (BisGMA, UDMA, BisEMA-6, TEGDMA), and C-8 alcohol derivatives were weighed into a MAX 20 plastic mixing cup having a screw cap (Flakteck, Landrum, S.C.). The cup was placed in an oven at 85° C. for 5 minutes and mixed in a DAC 150 FV speed mixer (Flakteck) for 1 minute at 3000 rpm. The filler component was then added and the cup was placed in an oven at 85° C. for 5 minutes and mixed in a DAC 150 FV speed mixer (Flakteck) for 1 minute at 3000 rpm. Heating at 85° C. for 5 minutes and subsequent mixing were repeated. Dental compositions (Examples 3-8) were prepared in this manner as paste composites and the relative amounts of components for each composite are listed in Table 1. For Comparative Example C4 the commercial product 3M FILTEK SUPREME Universal Restorative (3M Company) was used. These composite pastes (Examples 3-8 and Comparative Example C1) were evaluated for Watts shrinkage and Barcol hardness according to the Test Methods described herein. Evaluation results are provided in Table 2.

Example 9

2-Methyl-acrylic acid 2-([1,5]dithiocan-3-yloxycarbonylamino)-ethyl ester

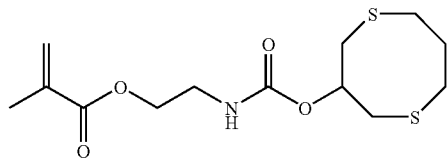

A mixture of 3-hydroxy-1,5-dithiacyclooctane (5.00 grams, 30 millimoles), 2-isocyanatoethyl methacrylate (4.72 grams, 30 millimoles), tetrahydrofuran (15 milliliters), and one drop of dibutyltin dilaurate were stirred at 55° C. for three hours. The solvent was then removed under reduced pressure and the crude product was purified by column chromatography over silica gel using a mixture of ethyl acetate/hexane (30/70). The product was isolated as a white solid (7.72 grams, 79% yield). Purity and structure verification of Example 9 were confirmed by ¹H NMR.

TABLE 1

| Ingredient (Parts by Weight) | Example 3 | Example 4 | Example 5 | Example 6 | Example 7 | Example 8 | Example C2 | Example C3 |
|---|---|---|---|---|---|---|---|---|
| BisGMA | — | 2.86 | — | 13.73 | 2.86 | 2.87 | — | 2.86 |
| BisEMA-6 | — | 4.01 | — | — | 4.01 | 4.02 | — | 4.01 |
| UDMA | — | 4.01 | 4.64 | 4.60 | 4.01 | 4.02 | — | 4.01 |
| TEGDMA | — | 0.57 | — | — | 0.57 | 0.57 | — | 0.57 |
| Ex. 1 | 22.92 | 11.45 | — | — | — | — | — | — |
| Ex. 2 | — | — | 18.33 | 4.64 | 11.45 | 11.48 | — | — |
| Ex. C1 | — | — | — | — | — | — | 22.91 | 11.46 |
| CPQ | 0.04 | 0.04 | 0.04 | 0.04 | 0.04 | 0.04 | 0.04 | 0.04 |
| EDMAB | 0.24 | 0.24 | 0.24 | 0.24 | 0.24 | 0.24 | 0.24 | 0.24 |
| DPIHFP | 0.12 | 0.12 | 0.12 | 0.12 | 0.12 | 0.12 | 0.12 | 0.12 |
| Filler A | 76.68 | 76.70 | 76.63 | 76.63 | 76.69 | 76.88 | 76.69 | 76.69 |
| TOTAL: | 100 | 100 | 100 | 100 | 100 | 100 | 100 | 100 |

TABLE 2

| Example | Watts Shrinkage (%) | Barcol Hardness Top | Barcol Hardness Bottom |
|---|---|---|---|
| 3 | 1.58 | 60 | 37 |
| 4 | 1.79 | 83 | 77 |
| 5 | 1.45 | 63 | 27 |
| 6 | 1.35 | 76 | 72 |
| 7 | 1.82 | 80 | 73 |
| 8 | 1.34 | 75 | 63 |
| C2 | 2.23 | 30 | 29 |
| C3 | 2.30 | 77 | 77 |
| C4 | 1.93 | 86 | 85 |

Comparative Example C5

2-Methyl-acrylic acid 2-(cyclooctyloxycarbonylamino)-ethyl ester

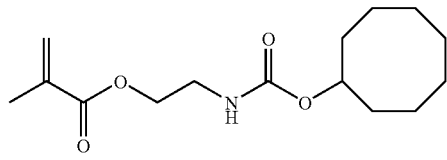

A mixture of cyclooctanol (3.00 grams, 23 millimoles), 2-isocyanatoethyl methacrylate (3.63 grams, 23 millimoles), methylene chloride (10 milliliters), and one drop of dibutyltin dilaurate were stirred at 50° C. for three hours. The solvent was then removed under reduced pressure and the crude product was purified by column chromatography over silica gel using a mixture of ethyl acetate/hexane (20/80). The product was isolated as an oil (5.20 grams, 80% yield). Purity and structure verification of Comparative Example C5 were confirmed by $^1$H NMR.

Examples 10-13 and Comparative Examples C6-C9

Dental compositions were prepared as described in Examples 3-8 using the relative amounts of components for each composite listed in Table 3. For Comparative Example C4 the commercial product 3M FILTEK SUPREME Universal Restorative (3M Company) was used. These composite pastes (Examples 10-13 and Comparative Examples C4 and C6-C9) were evaluated for Watts shrinkage and Barcol hardness according to the Test Methods described herein. Evaluation results are provided in Table 4.

TABLE 3

| Ingredient (Parts by Weight) | Example 10 | Example 11 | Example 12 | Example 13 | Example C6 | Example C7 | Example C8 | Example C9 |
|---|---|---|---|---|---|---|---|---|
| BisGMA | 9.16 | 11.46 | 13.75 | 16.04 | 9.16 | 11.45 | 13.75 | 16.04 |
| Ex. 3 | 13.75 | 11.45 | 9.16 | 6.87 | — | — | — | — |
| Ex. C2 | — | — | — | — | 13.75 | 11.45 | 9.16 | 6.87 |
| CPQ | 0.04 | 0.04 | 0.04 | 0.04 | 0.04 | 0.04 | 0.04 | 0.04 |
| EDMAB | 0.24 | 0.24 | 0.24 | 0.24 | 0.24 | 0.24 | 0.24 | 0.24 |
| DPIHFP | 0.12 | 0.12 | 0.12 | 0.12 | 0.12 | 0.12 | 0.12 | 0.12 |
| Filler A | 76.69 | 76.69 | 76.69 | 76.69 | 76.69 | 76.69 | 76.69 | 76.69 |
| TOTAL: | 100 | 100 | 100 | 100 | 100 | 100 | 100 | 100 |

TABLE 4

| Example | Watts Shrinkage (%) | Barcol Hardness Top | Barcol Hardness Bottom |
|---|---|---|---|
| 10 | 1.46 | 74 | 63 |
| 11 | 1.37 | 78 | 70 |
| 12 | 1.47 | 78 | 72 |
| 13 | 1.30 | 77 | 70 |
| C6 | 2.10 | 72 | 72 |
| C7 | 2.09 | 71 | 74 |
| C8 | 1.88 | 72 | 73 |
| C9 | 1.82 | 70 | 70 |
| C4 | 1.93 | 86 | 85 |

It can be seen from the results in Table 4 that the inventive dental composites (Examples 10-13) showed significantly improved shrinkage values in comparison with Examples C6-C9 containing Comparative Example C2 and the commercial FILTEK SUPREME restorative product while generally maintaining good to excellent hardness (Barcol hardness value).

The invention claimed is:

1. A curable composition comprising:
   a) a compound of the formula

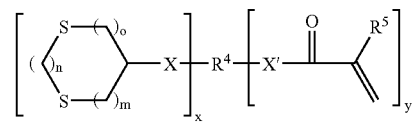

wherein X and X' are each independently an —O— or —NR$^1$—, where R$^1$ is an H or a C$_1$-C$_4$ alkyl group;
   each R$^5$ is independently an H, or a C$_1$-C$_4$ alkyl group,
   R$^4$ is an organic radical having a valence of x+y,
   n is 3 to 6,
   m is 1 to 3,
   o is 1 to 3,
   x and y are at least 1,
   one or more methylene groups on the ring may be substituted with C$_1$-C$_4$ alkyl group, and adjacent alkyl groups may be joined with the carbon atoms to which they are attached to form a carbocyclic ring, and
   b) an initiator.

2. The composition of claim 1 wherein n, m and o are numbers such that the ring has 8 to 9 ring atoms.

3. The composition of claim 1 wherein n is at least 3.

4. The composition of claim 1 wherein R$^4$ is selected from arylene, cycloalkylene and alkylene, said alkylene and arylene optionally further substituted by one or more catenary —O— or —NR$^1$— groups, and may further comprise a functional group selected from carbonyl, acyl, amide, urethane and urea.

5. The composition of claim 1, where x and y are 1.

6. The composition of claim 1 wherein said initiator is a photoinitiator.

7. The composition of claim 1 wherein said initiator is a redox initiator.

8. The composition of claim 6, wherein the photoinitiator comprises an electron donor, an iodonium salt, and a photosensitizer.

9. The composition of claim 8, wherein the photoinitiator comprises at least 0.04 wt-% of a photosensitizer.

10. The composition of claim 6, wherein the photoinitiator comprises a phosphine oxide capable of absorbing light in the range of about 300 to about 600 nm.

11. The composition of claim 1 wherein the composition further rises a filler.

12. The composition, of claim 1 further comprising a poly(meth)acryloyl compound.

13. The composition of claim 12, wherein the poly(meth)acryloyl compound is selected from the group consisting of ethoxylated bisphenol A dimethacrylate (BisEMA6), bisphenol A diglycidyl dimethacrylate (bisGMA), urethane dimethacrylate (UDMA), triethlyene glycol dimethacrylate (TEGDMA), glycerol dimethacrylate(GDMA), ethylenegylcol dimethacrylate, neopentylgylcol dimethacrylate (NPGDMA), and polyethyleneglycol dimethacrylate (PEGDMA).

14. The composition of claim 12 comprising:
a) 5 to 35 wt. % of said compound,
b) 0 to 20 wt. % of other mono(meth)acryloyl compounds, and
c) 65 to 95 wt. % of poly(meth)acryloyl compound,
based on the total weight of the unfilled composition.

15. The composition of claim 14 comprising 10 to 60 wt. % total monomers and 90 to 40 wt. % filler.

16. The composition of claim 15, which when cured, exhibits a Watts shrinkage of less than 2%.

17. The composition of claim 15, which when cured, exhibits a Barcol Hardness of at least 60.

18. A polymer composition comprising the polymerized composition of claim 14.

19. A method of preparing a dental restorative, the method comprising:
providing a curable dental composition of claim 1,
applying the composition to a tooth of a patient; and
curing the composition.

* * * * *

UNITED STATES PATENT AND TRADEMARK OFFICE
CERTIFICATE OF CORRECTION

PATENT NO. : 7,495,054 B2  Page 1 of 1
APPLICATION NO. : 11/229903
DATED : February 24, 2009
INVENTOR(S) : Kevin M. Lewandowski It is certified that error appears in the above-identified patent and that said Letters Patent is hereby corrected as shown below:

Column 20,
Line 22, after "specification." insert -- Unless otherwise indicated, all parts and percentages provided in the examples are on a weight basis, all water is deionized water, and all molecular weights are weight average molecular weight. --.

Lines 23-26, delete "Unless otherwise indicated, all parts and percentages provided in the examples are on a weight basis, all water is deionized water, and all molecular weights are weight average molecular weight.".

Column 26,
Line 65, delete "rises" and insert -- comprises --.
Line 66, delete "composition," and insert -- composition --.

Column 28,
Line 11, delete "1," and insert -- 1; --.

Signed and Sealed this

Sixteenth Day of June, 2009

JOHN DOLL
*Acting Director of the United States Patent and Trademark Office*